United States Patent [19]

Kyle et al.

[11] Patent Number: 5,521,158

[45] Date of Patent: * May 28, 1996

[54] PSEUDOPEPTIDE BRADYKININ RECEPTOR ANTAGONISTS

[75] Inventors: Donald J. Kyle, Abingdon; Babu J. Mavunkel, Baltimore, both of Md.

[73] Assignee: Scios Nova Inc., Mountain View, Calif.

[*] Notice: The portion of the term of this patent subsequent to Sep. 9, 2013, has been disclaimed.

[21] Appl. No.: 957,879

[22] Filed: Oct. 8, 1992

[51] Int. Cl.$^6$ .................................................... A61K 38/08
[52] U.S. Cl. ............................. 514/16; 530/329; 530/314
[58] Field of Search ....................... 514/15–16; 530/327, 530/328, 314

[56] References Cited

U.S. PATENT DOCUMENTS

| | | | |
|---|---|---|---|
| 4,242,329 | 12/1980 | Claeson et al. | 424/177 |
| 4,693,993 | 9/1987 | Stewart et al. | 514/14 |
| 4,801,613 | 1/1989 | Stewart et al. | 514/14 |
| 5,385,889 | 1/1995 | Kyle | 514/15 |

FOREIGN PATENT DOCUMENTS

| | | |
|---|---|---|
| 0370453A2 | 5/1990 | European Pat. Off. . |
| 0413277A1 | 11/1990 | European Pat. Off. . |

OTHER PUBLICATIONS

Journal of Medicine Chemistry, 1991, vol. 34, No. 8, pp. 2649–2653.

*Primary Examiner*—Christina Y. Chan
*Assistant Examiner*—David Lukton
*Attorney, Agent, or Firm*—Nath & Associates; Gary M. Nath; Suet M. Chong

[57] ABSTRACT

The invention relates to peptides of up to 10 amino acids that are synthesized by substituting at least one of the bradykinin amino acids found in positions 2, 3, 4 and 5 of the bradykinin peptide with a fatty acid amine. The modified bradykinin peptides produced confer increased resistance to enzymatic degradation and/or tissue specificity. The invention also relates to pharmaceutical preparations and processes of treatments using the modified bradykinin peptides.

14 Claims, No Drawings

PSEUDOPEPTIDE BRADYKININ RECEPTOR ANTAGONISTS

BACKGROUND OF THE INVENTION

1. Field of the Invention

This invention relates to compounds which are pseudopeptide bradykinin receptor antagonists, pharmaceutical compositions and methods for using these compounds to antagonize the effects of bradykinin in mammals, including humans. More particularly, the invention relates to the substitution of at least one of the bradykinin amino acids found in positions 2,3,4 and 5 with a fatty acid amine. The modified bradykinin antagonist confers increased resistance to enzymatic degradation and/or tissue specificity.

2. Description of the Prior Art

Bradykinin (BK), SEQ. ID No.: 1, is a nonapeptide generated as a result of the activity of kallikreins, a group of proteolytic enzymes present in most tissues and body fluids, on kininogens. Once released, kinins produce many physiological responses, including pain and hyperanalgesia by stimulating C- and A- fibers in the periphery. There is also considerable evidence that kinins contribute to the inflammatory process.

Bradykinin is overproduced in pathological conditions such as septic shock, anaphylaxis, rhinitis, asthma, inflammatory bowel disease, and certain other conditions including acute pancreatitis, post-gastrectomy dumping syndrome, carcinoid syndrome, migraine, and angioneurotic edema. The production of bradykinin from the plasma results in pain at the site of the pathological condition, and the overproduction intensifies the pain directly or via bradykinin-induced activation of the arachidonic acid pathway which produces prostaglandins and leukotrienes, the more distal and actual mediators of inflammation.

In addition to its analgesic and proinflammatory effects, bradykinin is a vasodilator. Because of its ability to lower blood pressure, bradykinin has been implicated in the pathogenesis of several shock syndromes, particularly septic or endotoxic shock. Bradykinin is also a potent bronchoconstrictor in animals and asthmatic subjects and it has been implicated as a contributor to the pathogenesis of airway inflammatory conditions such as allergic asthma and rhinitis.

Thus, a bradykinin inhibitor or bradykinin receptor antagonist is expected to possess a number of desirable biological effects in the treatment, for example, of inflammation, septic shock, asthma, burn pain, rhinitis, and allergy.

Several non-peptide, non-specific and non-selective antagonists of one or more of the biological activities of bradykinin have been described among compounds as diverse as analgesics and anti-inflammatory substances, which act via the prostaglandin system and not directly on bradykinin receptors. These are antihistamines; bradykinin-antibodies; benzodiazepine derivatives; high molecular weight ethylene oxide polymers; gallic acid esters; and serotonin inhibitors. None of these compounds or classes of compounds specifically inhibit the effects of bradykinin.

Heptyl esters of various amino acid-containing substances, such as single basic amino acids, the dipeptide Phe-Gly, and analogs of C- terminal peptide fragments of bradykinin (i.e., Pro-Phe-Arg) have been reported as anti-bradykinin substances. When tested in bradykinin assay systems, they prove to be weak partial agonists/antagonists, depending on the dose, with little specificity for inhibiting bradykinin action.

Several research groups have prepared bradykinin receptor antagonists. Stewart and Vavrek in U.S. Pat. No. 4,801,613, (which reference is incorporated herein in its entirety) disclose a series of bradykinin antagonists wherein the L-Pro at the 7-position of the peptide hormone bradykinin or other substituted analogs of bradykinin is substituted with an aromatic amino acid of the D-configuration which converts bradykinin agonists into bradykinin antagonists. The analogs produced are useful in treating conditions and diseases of a mammal and human in which an excess of bradykinin or related kinins are produced or injected as by insect bites into the body.

In U.S. Pat. No. 4,693,993, also to Stewart and Vavrek, additional L-Pro$^7$ substitution materials are disclosed.

U.S. Pat. No. 4,242,329 to Claeson et al. disclose the formation of bradykinin-inhibiting tripeptide derivatives. A process for producing said tripeptide derivatives by synthesis and purification methods which are known in peptide chemistry is also disclosed as well as pharmaceutical preparations comprising the tripeptide derivative.

Published European Patent Application No. 0 413 277 A1 to Hoechst A. G. discloses bradykinin antagonists containing the aromatic amino acid D-Phe at position 7 but containing unnatural amino acids at position 8 which impart increased potency.

Published European Patent Application No. 0 370 453 A2 to Hoechst A. G. discloses bradykinin antagonists containing a D-imino acid (D-Tic) at position 7.

Kyle et al. have recently reported bradykinin antagonist peptides which do not have an aromatic amino (or imino) acid at position 7 [Kyle, D. J. et al. *J. Med. Chem.* (1992), 34, 2649]. These peptides utilize ethers of D-4-hydroxyproline at position 7.

SUMMARY OF THE INVENTION

The present invention resides in the discovery that the novel compounds identified below, are potent bradykinin receptor antagonists. The compounds are useful in the treatment of various diseases including inflammatory disorders, asthma, septic shock, and burn pain. Included in the invention are pharmaceutical compositions containing the inventive compounds and methods of using the compounds as bradykinin receptor antagonists, More particularly, the invention relates to the modification of the sequence of the mammalian peptide hormone bradykinin (Arg-Pro-Pro-Gly-Phe-Ser-Pro-Phe-Arg), SEQ. ID NO.: 1, and pharmaceutically acceptable salts thereof, at the 2 through 5 amino acid residues in a unique manner which produces sequence-related analogues that act as specific and competitive inhibitors of the biological activities of bradykinin, The invention specifically relates to the substitution of at least one of the 2 to 5 amino acid residues with a material having the formula:

$$-N-(CH_2)_x-\overset{O}{\underset{\|}{C}}-$$

-AND- $$-N-(CH_2)_{x-1}-\overset{}{\underset{}{C}}-\overset{O}{\underset{\|}{C}}-\;\;\text{(with phenyl group)}$$

wherein

χ is 2 to 18;

and pharmaceutically acceptable salts thereof.

More specifically, the invention relates to the formation of peptides having the formula:

N-A-B-C-D-E-F-G-H-I-J-Cn wherein N is hydrogen;

A and B are independently selected from the group consisting of L-Arg, D-Arg, D-Gln, L-Gln, D-Asn, L-Asn, N-ε-acetyl-D-lysine, ε-acetyl-L-lysine, NG-p-tosyl-Arg, NG-nitro-Arg, Lys-Lys, acetyl-D-Arg, L-Citrulline, L-Lys, and D-Lys;

C is a direct bond or is selected from the group consisting of Pro, dehydro Pro, 4Hyp, Tic, Aoc, L-azetidine-2-carboxylic acid, Eac, Gly, Thz, Oic, Aib and R D is a direct bond or is selected form the group consisting of Pro, dehydroPro, 4Hyp, Tic, Aoc, L-azetidine-2-carboxylic acid, Eac, Gly, Thz, Oic Aib and R;

E is a direct bond or is selected from the group consisting of Gly, Ala, Thr, Ser and R;

F is a direct bond or selected from the group consisting of Phe, Thi, Leu, Ile, Tic, Oic, homoPhe, phenylGly, β-cyclohexylalanine, Nal, Val and R;

G is selected from the group consisting of Ser, Thr, 4Hyp, Gly, Val, and Ala;

H is a compound of the D-configuration and is selected from the group consisting of D-Tic, D-Phe and D-Hypethers selected from a material having the trans and D-configuration (*) and the formula:

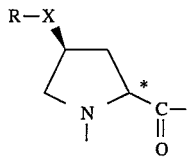

wherein

R is selected from the group consisting of $C_1-C_6$ alkyl, substituted $C_1-C_6$ alkyl, $C_2-C_8$ alkenyl, $C_3-C_8$ cycloalkyl, $C_3-C_8$ cycloalkyl substituted $C_1-C_6$ alkyl, an aryl group, a substituted aryl group, an arylalkyl group, and a group of the formula $R^1NHC(o)$— where $R^1$ is $C_1-C_6$ alkyl or aryl, and where X is either S or oxygen and is trans; and pharmaceutically acceptable salts thereof;

I is selected from the group consisting of Phe, Azt, Tic and Hypethers selected from a material having the L-configuration (*) and the formula:

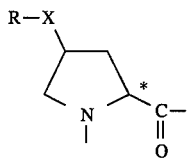

wherein

R is selected from the group consisting of $C_1-C_6$ alkyl, substituted $C_1-C_6$ alkyl, $C_2-C_8$ alkenyl, $C_3-C_8$ cycloalkyl, $C_3-C_8$ cycloalkyl substituted $C_1-C_6$ alkyl, an aryl group, a substituted aryl group, an arylalkyl group, and a group of the formula $R^1NHC(o)$—where $R^1$ is $C_1-C_6$ alkyl or aryl, and where X is S or oxygen, cis or trans and pharmaceutically acceptable salts thereof;

J is selected from the group consisting of Arg, Lys, Orn, Asn, Gln, N-ε-acetyl-Lys, and N-δ-acetyl-Orn;

Cn is a hydroxyl group or a C-terminal extension is selected from the group consisting of amide, alkoxy group, an acidic, basic or neutral aliphatic, aromatic, cyclic amino acid residue of the D- or L-configuration, and a peptide extension composed of D- or L-amino acids; and pharmaceutically acceptable salts thereof; and wherein R has the following formula wherein χ is 2 to 18;

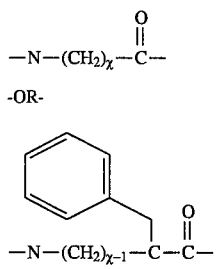

A particularly preferred material is a peptide wherein: N is hydrogen;

A and B are independently selected from the group consisting of L-Arg, D-Arg, Lys-Lys, Lys;

C is a direct bond or is selected from the group consisting of Pro, dehydroPro, 4Hyp and R;

D is a direct bond or is selected from the group consisting of Pro, dehydroPro, 4Hyp and R;

E is a direct bond or is Gly or R;

F is a direct bond or is selected from the group consisting of Phe, Thi, Leu, and β-cyclohexylalanine and R;

G is selected from the group consisting of Ser and Thr;

H is a compound of the D-configuration and is selected from the group consisting of D-Tic, D-Phe, and D-Hypethers selected from a material having the trans and D-configuration (*) and the formula:

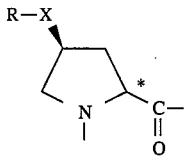

wherein

R is selected from the group consisting of $C_1-C_6$ alkyl, substituted $C_1-C_6$ alkyl, $C_2-C_8$ alkenyl, $C_3-C_8$ cycloalkyl, $C_3-C_8$ cycloalkyl substituted $C_1-C_6$ alkyl, an aryl group, a substituted aryl group, an arylalkyl group, and a group of the formula $R^1NHC(o)$—where $R^1$ is $C_1-C_6$ alkyl or aryl, and where X is either S or oxygen and is trans; and pharmaceutically acceptable salts thereof;

I is selected from the group consisting of Phe, Azt and Hypethers selected from a material having the L-configuration (*) and the formula:

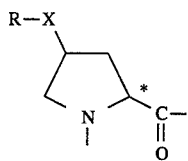

wherein

R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1$NHC(o)— where $R^1$ is $C_1$–$C_6$ alkyl or aryl, and where X is S or oxygen, cis or trans and pharmaceutically acceptable salts thereof;

J is selected from the group consisting of Arg and Lys;

Cn is a hydroxyl group;

and pharmaceutically acceptable salts thereof; and wherein R has the following formula wherein $\chi$ is 3 to 15;

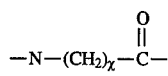

-OR-

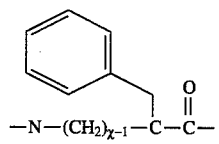

Another preferred material is a peptide wherein:

N is hydrogen;

A is D-Arg;

B is Arg;

C, D and E are direct bonds;

F is selected from the group consisting of

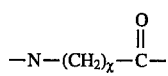

-AND-

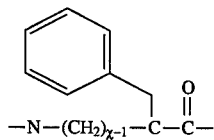

G is Ser;

H is selected from the group consisting of D-Tic and D-Phe;

I is selected from the group consisting of Phe, Azt, and Tic;

J is Arg;

Cn is a hydroxyl group;

and pharmaceutically acceptable salts thereof.

The present invention also includes a substituted bradykinin type peptide containing as an essential component a fatty acid amine selected from the group consisting of

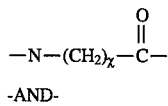

-AND-

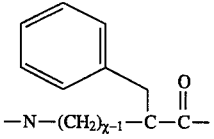

wherein $\chi$ is 2 to 18.

Additional embodiments involve a fatty acid amine derivative comprising

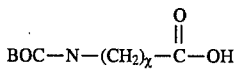

wherein $\chi$ is 2 to 18.

A further embodiment includes a fatty acid amine derivative comprising

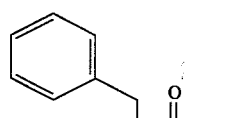
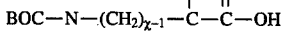

wherein $\chi$ is 2 to 18 and wherein the alpha carbon bond to the carbonyl moiety may be the R or S isomer.

Another embodiment of the invention involves a pharmaceutical composition useful as a bradykinin receptor antagonist comprising a pharmaceutical carrier and an effective amount of the novel bradykinin-type peptide. The invention also involves a process for antagonizing bradykinin receptor activity in mammals which comprises: administering to a subject an effective amount of the novel compound to antagonize bradykinin receptor activity.

A further embodiment involves a pharmaceutical preparation for treating local pain and inflammation from burns, wounds, cuts, rashes and other such trauma, and pathological conditions caused by the production of bradykinin or related kinins by an animal, which comprises: administering an effective amount of the novel peptide sufficient to antagonize bradykinin with a suitable pharmaceutical carrier. Another aspect of this invention involves a process for treating local pain and inflammation, which comprises: administering an effective amount of the pharmaceutical preparation to an animal in need thereof.

DETAILED DESCRIPTION OF THE INVENTION

Applicants' unexpectedly discovered that when the Arg-Pro-Hyp-Gly-Phe segment of the bradykinin antagonist DArg-Arg-Pro-Hyp-Gly-Phe-Ser-Tic-Oic-Arg was replaced with a pentaglycine moiety it resulted in an inactive peptide. However, the reintroduction of the phenylalanine resulted in regaining some receptor binding potency ($K_1$=321 nM), illustrating the importance of the lipophilic moiety at this position. The reintroduction of both phenylalanine and arginine to give DArg-Arg-Gly-Gly-Gly-Phe-Ser-DTic-Oic-Arg produced further improvement $K_i$=15 nM. Thus, it appears that a potent peptide bradykinin antagonist could be simplified while retaining most of its biological activity.

The present compounds which are bradykinin receptor antagonists have the following formula:

wherein

N is hydrogen;

A and B are independently selected from the group consisting of L-Arg, D-Arg, D-Gln, L-Gln, D-Asn, L-Asn, N-ε-acetyl-D-lysine, ε-acetyl-L-lysine, $N^G$-p-tosyl-Arg, $N^G$-nitro-Arg, Lys-Lys, acetyl-D-Arg, L-Citrulline, L-Lys, and D-Lys;

C is a direct bond or is selected from the group consisting of Pro, dehydroPro, 4Hyp, Tic, Aoc, L-azetidine-2-carboxylic acid, Eac, Gly, Thz, Oic, Aib and R;

D is a direct bond or is selected from the group consisting of Pro, dehydroPro, 4Hyp, Tic, Aoc, L-azetidine-2-carboxylic acid, Eac, Gly, Thz, Oic and Aib and R;

E is a direct bond or is selected from the group consisting of Gly, Ala, Thr, Ser and R;

F is a direct bond or selected from the group consisting of Phe, Thi, Leu, Ile, Tic, Oic, homoPhe, phenylGly, β-cyclohexylalanine, Nal, Val and R;

G is selected from the group consisting of Ser, Thr, 4Hyp, Gly, Val and Ala;

H is a compound of the D-configuration and is selected from the group consisting of D-Tic, D-Phe and D-Hypethers selected from a material having the trans and D-configuration (*) and the formula:

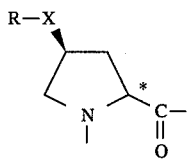

wherein

R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$—where $R^1$ is $C_1$–$C_6$ alkyl or aryl, and where X is either S or oxygen and is trans; and pharmaceutically acceptable salts thereof;

I is selected from the group consisting of Phe, Tic, Azt, Pip and Hypethers selected from a material having the L-configuration (*) and the formula:

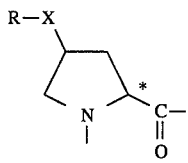

wherein

R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$—where $R^1$ is $C_1$–$C_6$ alkyl or aryl, and where X is S or oxygen, cis or trans and pharmaceutically acceptable salts thereof;

J is selected from the group consisting of Arg, Lys, Orn, Asn, Gln, N-ε-acetyl-Lys, and N-δ-acetyl-Orn;

Cn is a hydroxyl group or a C-terminal extension selected from the group consisting of amide, alkoxy group, an acidic, basic or neutral aliphatic aromatic, cyclic amino acid residue of the D- or L-configuration, and a peptide extension composed of D- or L-amino acids; and pharmaceutically acceptable salts thereof;

and wherein R has the following formula

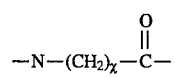

-AND-

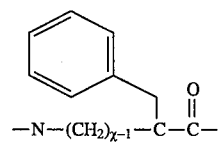

wherein

χ is 2 to 18;

Formula 2

Preferred compounds are those in which:

A and B are independently selected from the group consisting of L-Arg, D-Arg, Lys-Lys, Lys;

C is a direct bond or is selected from the group consisting of Pro, dehydroPro, 4Hyp and R;

D is a direct bond or selected from the group consisting of Pro, dehydroPro, 4Hyp and R;

E is a direct bond or is selected from the group consisting of Gly, and R;

F is a direct bond or is selected from the group consisting of Phe, Thi, Leu, β-cyclohexylalanine, and R;

G is selected from the group consisting of Ser, and Thr;

H is selected form the group consisting of D-Tic, D-Phe and D-Hypethers selected from a material having the trans and D-configuration (*) and the formula:

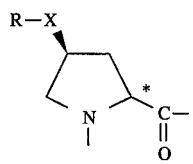

wherein

R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$—where $R^1$ is $C_1$–$C_6$ alkyl or aryl, and where X is either S or oxygen and is trans; and pharmaceutically acceptable salts thereof;

I is selected from the group consisting of Phe, Tic, Azt and Hypethers selected from a material having the L-configuration (*) and the formula:

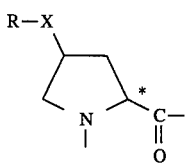

wherein
R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$—where $R^1$ is $C_1$–$C_6$ alkyl or aryl, and where X is S or oxygen, cis or trans and pharmaceutically acceptable salts thereof;

J is selected from the group consisting of Arg and Lys;
Cn is a hydroxyl group;
and pharmaceutically acceptable salts thereof; and wherein R has the following formula wherein χ is 2 to 18:

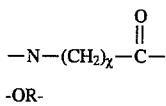

-OR-

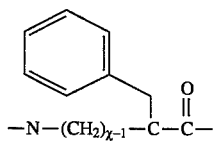

Formula 3
Most preferred are compounds wherein:
N is hydrogen;
A is D-Arg;
B is Arg;
C, D and E are direct bonds;
F is selected from the group consisting of

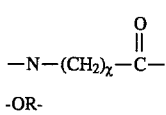

-OR-

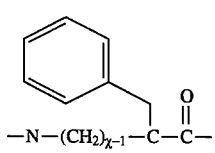

wherein
χ is 3 to 15
G is Ser;
H is D-Tic or D-Phe;
I is selected form the group consisting of Phe, Azt, and Tic;
J is Arg;
Cn is a hydroxyl group;
and pharmaceutically acceptable salts thereof.
Formula 4
Another preferred formulation is wherein:
A is D-Arg;
B is Arg;

C, D and E are direct bonds;
F is selected from the group consisting of

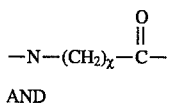

AND

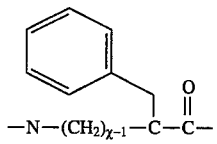

wherein
χ is 4 to 12
G is Ser;
H is selected from the group consisting of D-Tic and D-Phe;
I is selected from the group consisting of Tic, Azt and Phe;
J is Arg;
CN is a hydroxyl group;
and pharmaceutically acceptable salts thereof.
Formula 5
Preferred compounds have the formula selected from the group consisting of:

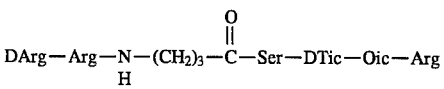

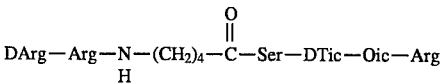

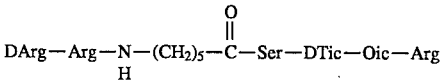

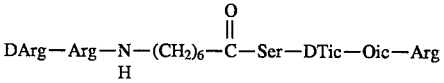

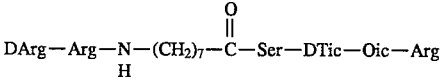

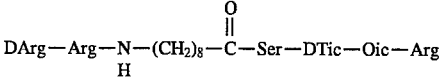

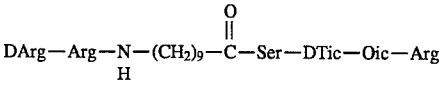

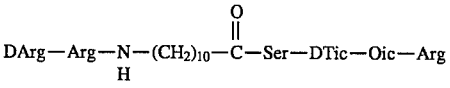

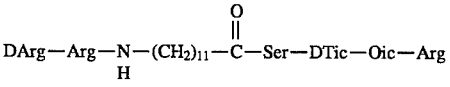

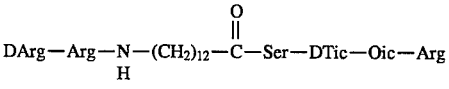

-continued

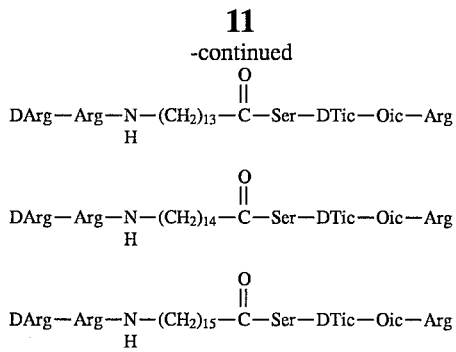

Formula 6

Other preferred compounds have the formula selected from the group consisting of:

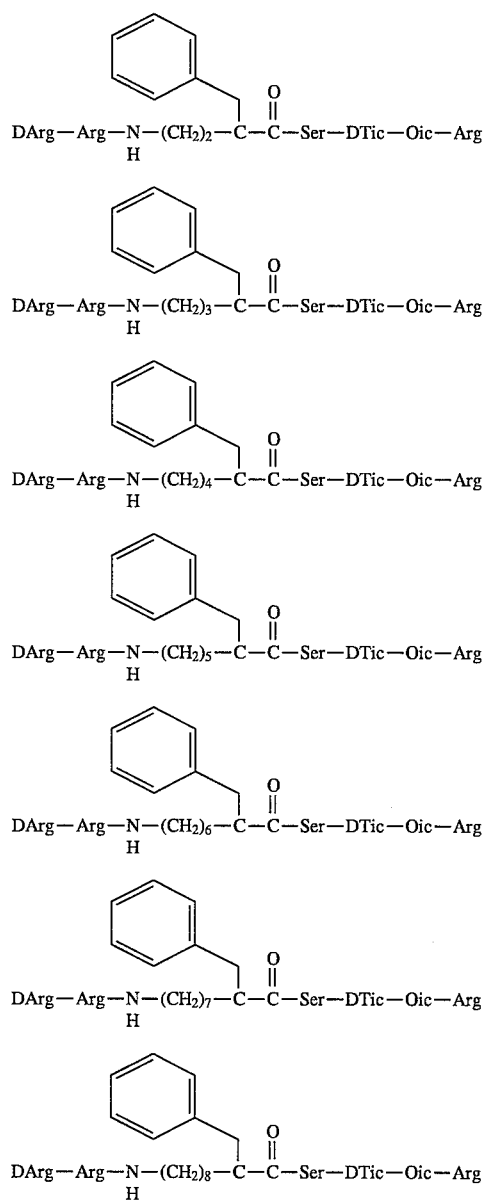

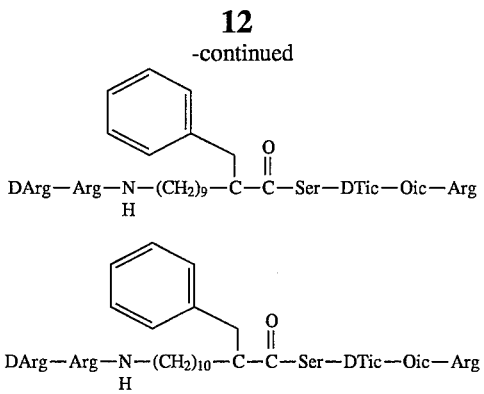

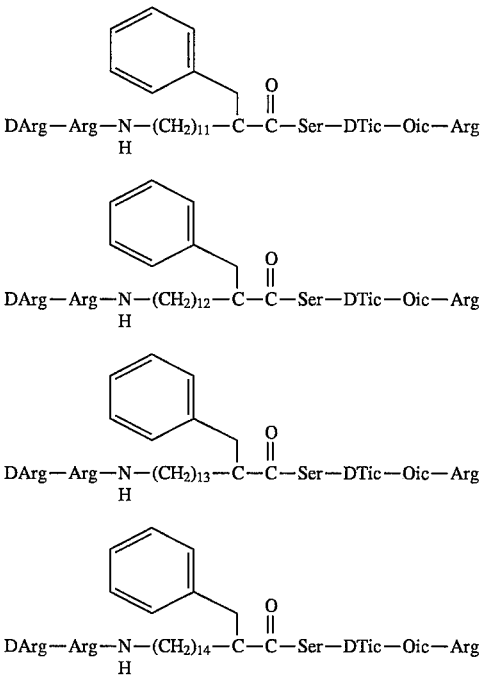

The bond between the carbonyl group and the alpha carbon containing the aromatic ring may be an R or S isomer.

Formula 7

Another preferred formulation involves a substituted bradykinin type peptide containing as an essential component a fatty acid amine selected from the group consisting of

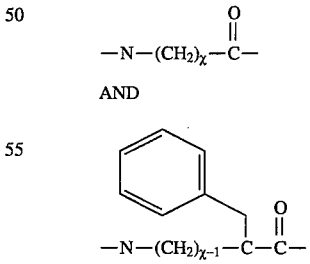

wherein $\chi$ is 2 to 18.

Formula 8

A further formulation involves a fatty acid amine derivative comprising

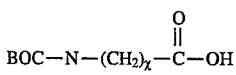

wherein

χ is 2 to 18.
Formula 9

An additional fatty acid amine derivative comprises

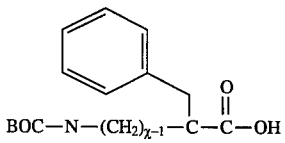

wherein

χ is 2 to 18.

As used in the specification and claims, "alkyl" is a paraffinic hydrocarbon group which may be derived from an alkane by dropping one hydrogen from the formula, such as methyl, ethyl, propyl, isopropyl, butyl, and so forth; "substituted $C_1-C_6$ alkyl" is a branched alkyl, such as methyl butyl; "aryl" is an aromatic ring compound such as benzene, phenyl, naphthyl; "substituted aryl" is a substituted aromatic ring, such as nitro substitution, halogen substitution or alkyl substitution on the aromatic ring; and "aralkyl" is an aryl being attached through an alkyl chain, straight or branched, containing from one through six carbons, such as a phenylpropyl group. A "direct bond" is a bond which replaces a particular or group of amino acid compound(s) between adjacent amino acids and which amino acid may also be indicated to be absent by the term "null". The phrase "a suitable amine protecting group" is a group, such as BOC (t-butyloxy-carbonyl-) protecting group which protects the amine moiety from reaction and which can be removed under mild conditions so as not to affect the rest of the molecule.

While the R and S isomers are useable in this invention, the S-configuration of the compounds of the invention are the most preferred structures.

Definitions of the amino acid abbreviations used herein are as follows:

Arg is arginine; Ala is alanine; Aib is 2-aminoisobutyric acid; Aoc is (S,S,S)-2-azabicyclo[3.3.0]octane-3-carboxylic acid; Asn is asparagine; Azt is azetidine-2-carboxylic acid; Eac is ε-aminocaproic acid; Gln is glutamine; Gly is glycine; Ile is isoleucine; Leu is leucine; Lys is lysine; Met is methionine; Nal is beta-2-naphthylalanine; Orn is ornithine; Pro is proline; dehydroPro is 3,4-dehydroproline; homoPhe is homophenylalanine; 4Hyp is 4-hydroxyproline; Ser is serine; Sar is sarcosine; Thi is beta-2-thienylalanine; Thr is threonine; Thz is thiazolidine-4-carboxylic acid; Phe is phenylalanine; Pip is homoproline; phenylGly is 2-phenylglycine; Tic is tetrahydroisoquinoline-3-carboxylic acid; Oic is (2S, 3aS, 7aS)-octahydro-1H-indole-2-carboxylic acid; Val is valine. Furthermore, prenyl is a 3-methyl-2- butenyl radical.

Aoc can be prepared by the method of V. Teetz, R. Geiger and H. Gaul, *Tetrahedron Lett.* (1984), 4479. Tic can be prepared by the method of K. Hayashi, Y. Ozaki, K. Nunami and N. Yoneda, *Chem. Pharm. Bull.* (1983) 31, 312.

All amino acids residues, except Gly, and Sar, described in the specification are preferably of the L-configuration unless otherwise specified. It should be recognized, however, that the 7 position (H) must always be the D-configuration. The symbols and abbreviations used for amino acids, their derivatives and protecting groups, and peptides and their salts are those customarily used in peptide chemistry. (See *Biochem. J.* (1972), 126, 773), which Journal reference is hereby incorporated by reference).

Table I shows the general location of the amino acid groups as used herein.

TABLE I

| N— | A— | B— | C— | D— | E— | F— | G— | H— | I— | J— | Cn | (formula) |
|---|---|---|---|---|---|---|---|---|---|---|---|---|
| | Arg— | Pro— | Pro— | Gly— | Phe— | Ser— | Pro— | Phe— | Arg | | | Bradykinin (SEQ ID NO: 1) |
| | 1 | 2 | 3 | 4 | 5 | 6 | 7 | 8 | 9 | | | (position number) |

Exemplary Boc protected amino acids include the following nonlimiting materials:

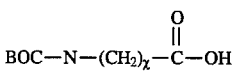

-AND-

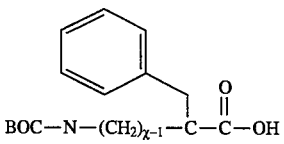

wherein

χ is 2 to 18

The synthesis of the peptides of this invention including derivation, activation, and coupling of protected amino acid residues, and their purification, and the analytical methods for determining identity and purity are included in the general body of knowledge of peptide chemistry, as described in Houben Weyl *Methoden der Organischen Chemie*, (1974), Vol. 16, parts I & II for solution-phase synthesis, and in *Solid Phase Peptide Synthesis*, (1984), by Stewart and Young for synthesis by the solid-phase method of Merrifield.

Any chemist skilled in the art of peptide synthesis can synthesize the peptides of this invention by standard solution methods or by manual or automated solid phase methods.

Two nonpeptide bradykinin antagonists were prepared by the following procedures.

Preparation of α-(3-Aminopropyl)-benzenepropionic acid (1)

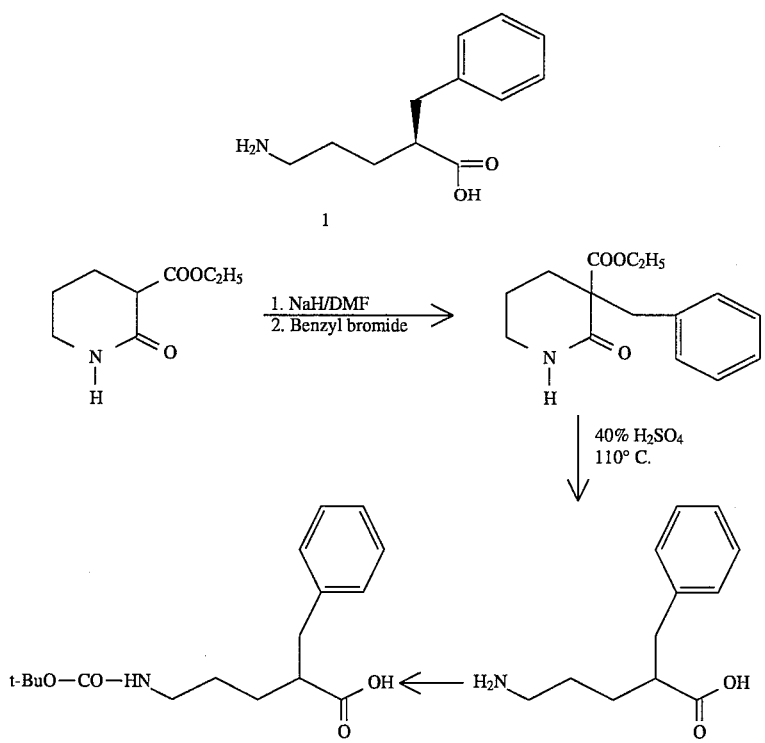

α-(3-Aminopropyl)-benzenepropionic acid (1) is expected to replace the Gly-Phe segment of the bradykinin antagonist DArg-Arg-Pro-Hyp-Phe-Ser-Tic-Oic-Arg. This amino acid, if it sustains the receptor binding activity, would eliminate the amide bond between glycine and phenylalanine. 2-Substituted-15-aminovaleric acids have been prepared by the hydrolysis of 3-substituted-3(ethyoxycarbonyl)-2-piperidones by the procedure of Kikumoto et al. (to Mitsubishi Chemical Industries Co., Ltd) JP 52083602, Jul. 12, 1977. (See Scheme 1).

However, this method provides only a recemic mixture. Therefore, either separation of the enantiomers by salt formation and selective recrystallization or an enantioselective synthesis is required to obtain the desired S isomer. The process of synthesizing this compound (Scheme 2) can be exemplified using the Evans technology (Evans, D. A., Ennis, M. D.; Mathre, D. J. Asymmetric Alkylation Reactions of Chiral Imide Enolates. A Practical Approach to the Enantioselective Synthesis of a α-Substituted Carboxylic Acid Derivatives. *J. Am. Chem. Soc.* 1982, 104, 1737–1739.)

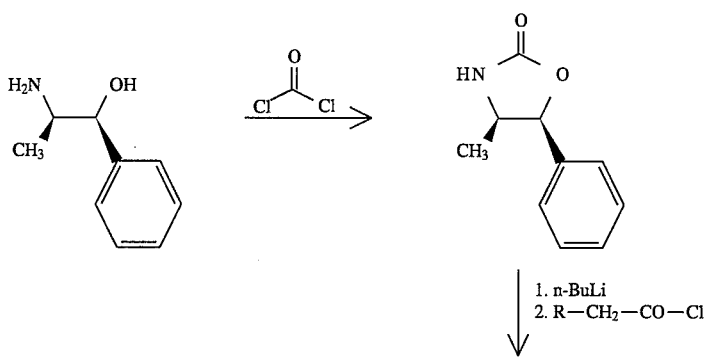

-continued
Scheme 2

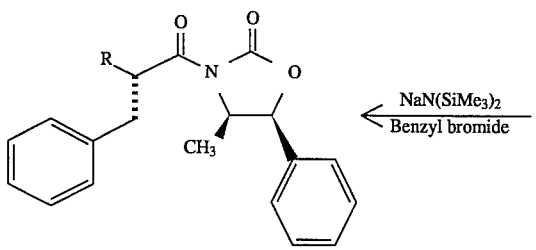 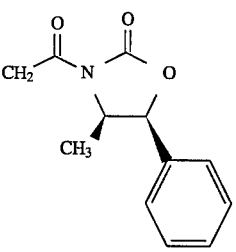

6
R = —(CH₂)₃—NH₂ where the amino group is properly protected.

The preparation of compounds for administration in pharmaceutical preparations may be performed in a variety of methods well known to those skilled in the art. Appropriate pharmaceutically acceptable salts within the scope of the invention are those derived from mineral acids such as hydrochloric acid, hydrobromic acid, phosphoric acid, nitric acid and sulfuric acid; and organic acids such as tartaric acid, fumaric acid, lactic acid, oxalic acid, ethylsulfonic acid, citric acid, methanesulfonic acid, benzenesulfonic acid, p-toluenesulfonic acid, and the like, giving the hydrochloride, sulfate, phosphate, nitrate, methanesulfonate, tartrate, benzenesulfonate, p-toluensulfonate, and the like, salt, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc and the like.

Salts may also be formed with suitable organic bases. Bases suitable for the formation of pharmaceutically acceptable base addition salts with compounds of the present invention include organic bases which are non-toxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di-, and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See example, "Pharmaceutical Salts," *J. Pharm. Sci.* (1977) 66(1): 1–19).

The compounds of the invention may contain an asymmetric carbon atom. Thus, the invention includes the individual stereoisomers, and the mixtures thereof. The individual isomers may be prepared or isolated by methods known in the art.

Therapeutic applications of the novel bradykinin antagonists include not only treatment for the production of bradykinin or related kinins by the animal but also the injection of bradykinin related peptides into an animal as a result of bites and stings. Topical application alone or in combination with subcutaneous utilization of the bradykinin antagonists of the invention can be employed to treat the effects of bradykinin-related peptides causing pain, inflammation and swelling.

The therapeutic use of bradykinin antagonists of this invention for other traumatic inflammatory or pathological conditions which are known to be mediated by bradykinin or exacerbated by an overproduction of bradykinin can also be achieved. These conditions include local trauma such as wounds, burns and rashes, angina, arthritis, asthma, allergies, rhinitis, shock, inflammatory bowel disease, low blood pressure, and systemic treatment of pain and inflammation.

In parenteral administration of the novel compounds and compositions of the invention the compounds may be formulated in aqueous injection solutions which may contain antioxidants, buffers, bacteriostats, etc. Extemporaneous injection solutions may be prepared from sterile pills, granules or tablets which may contain diluents, dispersing and surface active agents, binders and lubricants which materials are all well known to the ordinary skilled artisan.

In the case of oral administration, fine powders or granules of the compound may be formulated with diluents and dispersing and surface active agents, and may be prepared in water or in a syrup, in capsules or cachets in the dry state or in a non-aqueous suspension, where a suspending agent may be included. The compounds may also be administered in tablet form along with optional binders and lubricants, or in a suspension in water or syrup or an oil or in a water/oil emulsion and may include flavoring, preserving, suspending, thickening, and emulsifying agents. The granules or tablets for oral administration may be coated and other pharmaceutically acceptable agents and formulations may be utilized which are all known to those skilled in the pharmaceutical art.

Solid or liquid carriers can also be used. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Ointments and creams are prepared using various well known hydrophilic and hydrophobic bases. Topical reservoirs suitably are prepared using known polymeric materials such as various acrylic-based polymers selected to provide desired release characteristics. Suppositories are prepared from standard bases such as polyethylene glycol and cocoa butter.

The method of treatment according to this invention comprises administering internally or topically to a subject an effective amount of the active compound. Doses of active compounds in the inventive method and pharmaceutical compositions containing same are an efficacious, nontoxic quantity selected from the range of 0.01 to 100 mg/kg of active compound, preferably 0.1 to 50 mg/kg. Persons skilled in the art using routine clinical testing are able to determine optimum doses for the particular ailment being treated. The desired dose is administered to a subject from 1 to 6 or more times daily, orally, rectally, parenterally, topically, or by inhalation.

The efficacy of the inventive compounds of this invention as bradykinin receptor antagonists can be determined using bradykinin binding and tissue assays. The results of these assays demonstrate that the novel compounds are potent, selective bradykinin receptor antagonists.

The following examples are illustrative of preferred embodiments of methods of preparating the compounds of the invention and are not to be construed as limiting the invention thereto.

EXAMPLE 1

SYNTHESIS OF N-BOC-5-AMINO-2-(S)-BENZYL PENTANOIC ACID

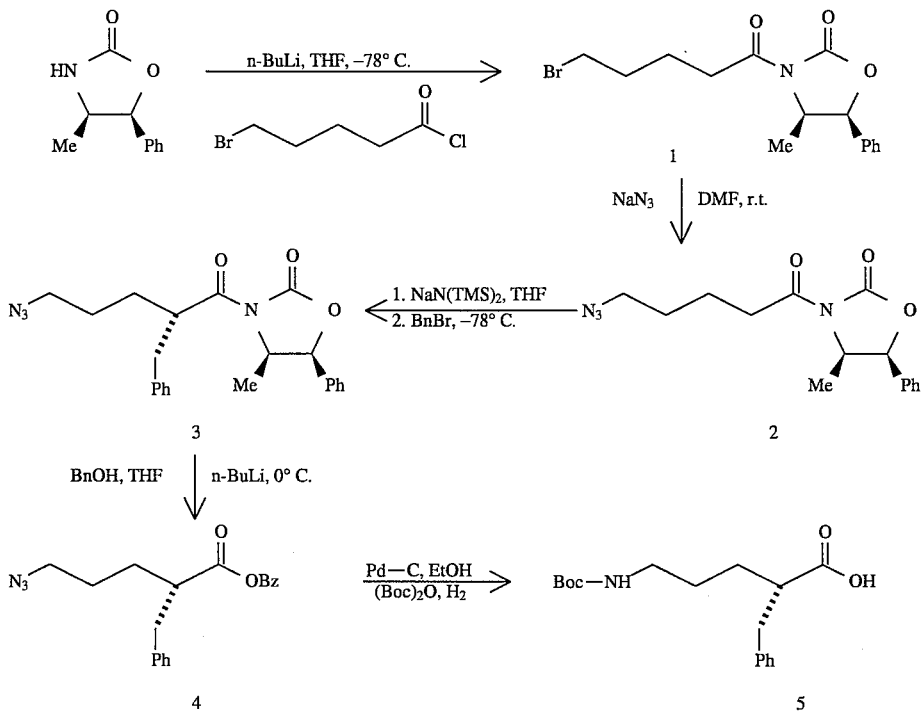

1. Preparation of 1-(5-bromopentanoyl )-5-(R)-methyl-4-(R)-phenyloxazolidone 1.

To a solution of 5-(R)-methyl-4-(R)-phenyloxazolidone[1] (5.00 g, 28.2 mmol) in THF (50 ml) at -78° C. n-BuLi (33.89 mmol, 1.6M in hexane) was added dropwise to give a brown solution. The solution was stirred at −70° C. for 30 min and 5-bromovaleryl chloride (29.66 mmol ) was added slowly. After the mixture was stirred at −78° C. for 40 min, it turned yellow. Saturated aqueous ammonium chloride (50 ml) was added to the mixture, and THF was removed. The organic material was extracted with ethyl acetate (3×100 ml). The combined ethyl acetate extracts were washed with brine (100 ml), and dried over sodium sulfate. A white solid was obtained upon removal of the solvent (8.89 g, 98%). This solid was used for the next step without further purification. The analytical sample was obtained by recrystallation from hexane, m.p.: 68°–69° C.

IR (KBr, cm$^{-1}$): 2944, 1776, 1702, 1355, 1195, 669.

$^1$H NMR (δ, CDCl$_3$: 0.90 (d, J=6.5 Hz, 3H), 1.84 (m, 2H), 1.94 (m, 2H), 2.98 (m, 2H), 3.43 (t, J=9.6 Hz, 2H), 4.76 (m, 1H), 5.67 (d, J=7.3 Hz, 1H), 7.35 (m, 5H).

2. Preparation of 1-(5-Azido-pentanoyl)-5-(R)-methyl-4-(R)-phenyloxazolidone 2.

A solution of bromopentanoyloxazolidone 1 (5.62 g, 17.35 mmol) and sodium azide (1.113 g, 17.35 mmol) in DMF (25 ml) was stirred at room temperature (25° C.) for 5 hr. Water (200 ml) was added, and the mixture was extracted with ethyl acetate (3×150 ml). The combined ethyl acetate extracts were washed with water (100 ml), brine (100 mol), and dried over sodium sulfate. A yellow oil obtained upon removal of the solvent was purified by column chromatography (ETOAc:hexane=1:9) to afford a white solid (4.45 g, 90%). The analytical sample was obtained by recrystallization from hexane, m.p.: 71°–72° C.

IR (KBr, cm$^{-1}$): 2944, 2872, 2100, 1774, 1707.

$^1$H NMR (δ, CDCl$_3$): 0.90 (d, J=6.5 Hz, 3H), 1.75 (m, 4H), 2.95 (m, 2H), 3.33 (t, J=7.1 Hz, 2H), 4.76 (m, 1H), 5.67 (d, J=7.3 Hz, 1H), 7.36 (m, 5H).

3. Preparation of 1-[5-Azido-2-(S)-benzyl-pentanoyl]-5-(R)-methyl-4-(R)-phenyloxazolidone 3.

To a solution of azidopentanoyloxazolidone (4.45 g, 15.56 mmol) in THF (100 ml) at −78° C., sodium bis(trimethylsilyl) amide (18.67 mmol, 1M in THF) was added and the solution was stirred at −78° C. for 30 min. Benzyl bromide (46.67 mmol) was added and the mixture was stirred at −78° C. for another 4 hr. TLC (EtOAc:hexane=1:9) indicated that the reaction was completed. Saturated aqueous ammonium chloride (80 ml) was added and THF was removed. The organic material was extracted with ethyl acetate (3×180 ml). The combined ethyl acetate extracts were washed with brine (100 ml), and dried over sodium sulfate. A light orange oil obtained upon removal of the solvent was purified by column chromatography (EtOAc:hexane=1.9) to afford a pale yellow oil (4.16 g, 71%). $^1$H NMR analysis indicated that it was a single diasteroisomer. [α]D=+39° (c=1.0, CH$_2$Cl$_2$).

IR (film, cm$^{-1}$): 2936, 21000, 1782, 1699, 1604, 1455, 1221, 763, 701.

$^1$H NMR (δ, CDCl$_3$): 0.64 (d, J=6.5 Hz, 3H), 1.59 (m, 3H), 1.86 (m, 1H), 2.76 (dd, J=13.3, 7.4 Hz, 1H), 3.03 (dd, J=13.3, 7.6 Hz, 1H), 3.26 (t, J=6.7 Hz, 2H), 4.25 (m, 1H), 4.75 (m, 1H), 5.62 (d, J=7.4 Hz, 1H), 7.25 (m, 10H).

4. Preparation of benzyl 5-azido-2-(S)-benzylpentanoate 4.

To a solution of benzyl alcohol (11.02 mmol) in THF (50 ml) at 0° C. in a ice bath, n-BuLi (8.2 mmol, 1.6M in hexane) was added. The solution was stirred at 0° C. for 10 min. A solution of 5-azido-2-(S)-benzyl-pentanoyloxazolidone 3 (2.16 g, 5.5 mmol) in THF (20 ml) was added and the mixture was stirred at 0° C. for 1 hr. TLC (EtOAc:hexane= 2:8) showed that the reaction was completed. Saturated aqueous ammonium chloride (25 ml) was added, and THF was removed. The organic material was extracted with ethyl acetate (3×150 ml). The combined ethyl acetate layers were washed with brine (100 ml), and dried over sodium sulfate. A pale yellow oil obtained upon removal of the solvent was purified by column chromatography (ETOAc:hexane=5:95) to afford a pale yellow oil (1.54 g, 90%). [α]D=+5.9° (c=1.0, CH$_2$Cl$_2$).

IR (film, cm$^{-1}$): 3028, 2946, 2103, 1735, 1604, 1496, 1452, 748, 701.

$^1$H NMR (δ, CDCl$_3$): 1.58 (m, 3H), 1.71 (m, 1H), 2.77 (m, 2H), 2.95 (m, 1H), 3.24 (t, J=6.5 Hz, 2H), 5.17 (s, 2H), 7.21 (m, 10H).

5. Preparation of N-Boc-5-amino-2(S)-benzylpentanoic acid 5.

A mixture of benzyl 5-azido-2-(S)-benzylpentanoic 4 (2.10 g, 6.75 mmol), catalytic amount of 10% palladium-on-carbon and di-tert-butylcarbonate (2.95 g, 13.5 mmol) in ethanol (50 ml) was taken in a hydrogenator at 60 psi and stirred for 14 hr. The solution was filtered and ethanol was removed to afford a colorless oil. The title compound was purified by column chromatography (ETOAc:hexane=3:7) to give an oil (1.01 g, 49%). [α]D=+7.9° (c=1.0, CH$_2$Cl$_2$).

IR(film, cm$^{-1}$): 3342, 2936, 1715, 1519, 1435, 1368, 1252, 1167, 699.

$^1$H (6, CDCl$_3$): 1.41 (m, 9H), 1.52 (m, 3H), 1.65 (m, 1H), 2.70 (m, 2H), 3.00 (m, 1H), 3.12 (m, 2H), 4.55 (br s, 1H), 7.20 (m, 5H).

$^{13}$C NMR (6, CDCl$_3$): 27.2 (—CH$_2$), 28.4 (—CH$_3$), 28.7 (—CH$_2$), 38.1 (—CH$_2$), 40.2 (—CH$_2$ ), 46.9 (—CH), 80.0 (—C—), 126.4 (—CH), 128.4 (—CH), 128.9 (—CH), 139.0 (=C=), 156.0 (O=C—NH), 180.0 (—COOH).

EXAMPLE 2

SNYTHESIS OF N-BOC-11-AMINO-2-(S)-BENZYL-UNDECANOIC ACID

Scheme II

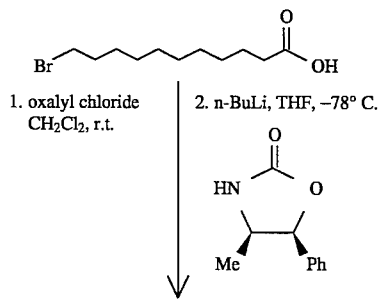

-continued
Scheme II

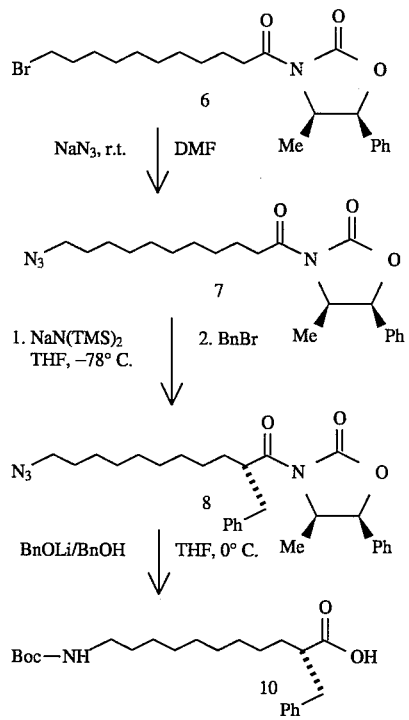

1. Preparation of 1-(11-Bromo-undecanoyl)-5-(R)-methyl-4-(R)-phenyloxazolidone 6.

To a solution of 11-bromoundecanoic acid (28.2 mmol) in methylene chloride (80 ml) at 0° C. oxalyl chloride (70.6 mmol) and a few drops of pyridine were added. The solution was stirred at room temperature (25° C.) for 2 hr. The solvent was removed and the residue was dried under high vaccuum for 2 hr. The resulting yellow liquid in THF (50 ml) was identified as solution A.

To a solution of 5-(R)-methyl-4-(R)-phenyl oxazolidone$^1$ (5.00 g, 28.2 mmol) in THF (50 ml) at -78° C., n-BuLi (33.8 mmol, 1.6M in hexane) was added dropwise and the resulting yellow solution was stirred at -78° C. for 30 min and identified as solution B. Solution A was added to solution B, and the resulting slurry was stirred at -78° C. for 1 hr. Saturated aqueous ammonium chloride was added and THF was removed. The organic material was extracted with ethyl acetate (3×150 ml). The combined ethyl acetate extracts were washed with brine (100 ml), and dried over sodium sulfate. A white solid was obtained upon removal of the solvent (11.97 g, 100%). The analytical sample was recrystallized from hexane, m.p.: 73°-74° C.

IR (KBr, cm$^{-1}$): 2923, 2856, 1794, 1705. 1355.

$^1$H NMR (δ, CDCl$_3$): 0.85 (d, J=6.5 Hz, 3H), 1.27 (m, 12H), 1.68 (m, 2H), 1.80 (m, 2H), 2.92 (m, 2H), 3.40 (t, J=7.5 Hz, 2H), 4.76 (m, 1H), 5.66 (d, J=7.3 Hz, 1H), 7.35 (m, 5H).

2. Preparation of 1-(11-Azido-undecanoyl)-5-(R)-methyl-4(R)-phenyloxazolidone 7.

A solution of bromoundecanoyl oxazolidone 6 (8.00 g, 18.48mmol) and sodium azide (6.00 g, 92.4 mmol) in DMF (30 ml) was stirred at room temperature for 20 hr. Water (200 ml) was added and the organic material was extracted with ethyl acetate (3×150 ml). The combined ethyl acetate extracts were washed with water (100 ml), brine (100 ml), and dried over sodium sulfate. A white solid was obtained upon removal of the solvent. The title compound was purified by column chromatography (EtOZc:hexane=1:9) to afford a white solid (5.07 g, 70%). The analytical sample was obtained by recrystallization from hexane, m.p.: 53°–54° C.

IR (KBr, cm$^{-1}$): 2915, 2103, 1769, 1702, 1360, 1203.

$^1$H NMR (δ, CDCl$_3$) 0.89 (d, J=6.5 Hz, 3H), 1.30 (m, 12H), 1.62 (m, 4H), 2.94 (m, 2H), 3.25 (t, J=7.0 Hz, 2H), 4.76 (m, 1H), 5.66 (d, J=7.3 Hz, 1H), 7.35 (m, 5H).

3. Preparation of 1-[11-Azido-2(S)-benzylundecanoyl]-5-(R)-methyl-4-(R)-phenyl-oxazolidone 8.

To a solution of azidoundecanoyloxazolidone 7 (3.25 g, 8.4 mmol) in THF (60 ml) at −78° C. sodium bis(trimethylsilyl) amid (10 mmol, 1M in THF) was added. The mixture was stirred at −78° C. for another 3 hr. Saturated aqueous ammonium chloride (50 ml) was added and THF was removed. The organic material was extracted with ethyl acetate (3×150 ml)). The combined ethyl acetate extracts were washed with brine (100 ml), and dried over sodium sulfate. A yellow liquid was obtained upon removal of the solvent. HPLC indicated that the ratio of two diastereomers was 98:2. The title compound was purified by column chromatography (EtOAc:hexane=5:95) to afford a pale oil (3.26 g, 82%). $^1$H NMR analysis indicated that it was a single diasterioisomer. [α]$_D$=+29.0° (C=1.0, CH$_2$Cl$_2$).

IR (film, cm$^{-1}$) 2926, 2856, 2095, 1779, 1699, 1604, 1455, 1344, 1195, 699.

$^1$H NMR (δ, CDCl$_3$): 0.61 (d, J=6.7 Hz, 3H), 1.26 (m, 12H), 1.65 (m, 4H), 2.77 (dd, J=13.3, 7.0 Hz, 1H), 2.99 (dd, J=13.3, 8.1 Hz, 1H), 3.25 (t, J=7.0 Hz, 2H), 4.25 (m, 1H), 4.73 (m, 1H), 5.59 (d, J=7.3 Hz, 1H), 7.28 (m, 10H).

4. Preparation of benzyl 11-azido-2-(S)-benzylundecanoate 9.

To a solution of benzyl alcohol (21.84 mmol) in THF (50 ml) at 0° C. n-BuLi (16.38 mmol, 16M in hexane) was added, and the solution was stirred at 0° C. for 30 minutes. A solution of azido-2-(S)-benzylundecanoyloxazolidone 8 (5.20 g, 10.92 mmol) in THF (50 ml) was added and the mixture was stirred at 0° C. for 3 hr. Saturated aqueous ammonium chloride (50 ml) was added and THF was removed. The organic material was extracted with ethyl acetate (3×150 ml). The combined ethyl acetate extracts were washed with brine (100 ml), and dried over sodium sulfate. A light yellow liquid was obtained upon removal of the solvent. This material was purified by column chromatography (EtOAc:hexane =5:95) to afford a colorless oil (4.01 g, 90%). [α]$_D$=+8.9° (c=1.0, CH$_2$Cl$_2$).

IR (film, Cm$^{-1}$): 2928, 2856, 2113, 1735, 1455, 1257, 1151, 699.

$^1$H NMR (δ, CDCl$_3$): 1.22 (m, 12H), 1.55 (m, 4H), 2.75 (m, 2H), 2.94 (m, 1H), 3.24 (t, J=6.5 Hz, 2H), 5.03 (s, 2H), 7.26 (m, 10H).

5. Preparation of N-Boc-11-amino-2-(S)-benzylundecanoic acid 10.

A mixture of benzyl 11-azido-(S)-benzylundecanoate 9 (3.80 g, 9.3 mmol), di-tert-butyl carbonate (4.08 g, 18.6 mmol) and catalytic amount of 10% palladium-on-carbon in ethanol (50 ml) was taken in a hydrogenator at 60 psi and stirred for 20 hr. The mixture was filtered and ethanol was removed to give an oil which was purified by column chromatography (EtOAc:hexane=3:7) to afford an oily product (1.91 g, 52%). [α]$^D$=+7.6° (C=1.0, CH$_2$Cl$_2$).

IR (film, cm$^{-1}$): 3340, 2926, 2859, 1709, 1517, 1368, 1249, 1170.

$^1$H NMR (δ, CDCl$_3$): 1.25 (m, 13H), 1.42 (m, 12H), 1.60 (m, 1H), 2.65 (m, 1H), 2.74 (dd, J=13.5, 6.4 Hz, 1H), 2.97 (dd, J=13.5, 7.7 Hz, 1H), 3.10 (m, 2H), 4.60 (br s, 1H), 7.20 (m, 5H). $^{13}$C NMR (δ, CDCl$_3$): 26.73 (—CH$_2$—), 27.14 (—CH$_2$—), 28.44 (—CH$_3$), 29.22 (—CH$_2$—), 29.32 (—CH$_2$—), 29.9(—CH$_2$—), 31.71 (—CH$_2$—), 38.19 (—CH$_2$—), 40.51 (—CH$_2$—), 47.37 (—CH—), 79.00 (13 C—), 126.32 (—CH—), 128.39 (—CH—), 128.91 (—CH—), 139.30 (=C=), 156.00 (—CO—NH), 180.86 (—COOH).

General Procedure for Automated Peptide Synthesis:

The peptide was synthesized employing t-Boc chemistry on a solid phase synthesizer (Milligen Biosearch 9600 Peptide Synthesizer). Boc-Arg(Tos)-PAM resin (Applied Biosystems) (PAM=phenylacetamidomethyl), 0.25 g, with a resin substitution of 0.62 mmol Arg/gram of resin, was placed in the reaction vessel and subjected to Procedure A for the coupling of Boc-Oic. Commercially available amino acids were purchased from Bachem Bioscience. Volumes of reagents and solvents were approximately 20 ml/gram of resin.

Procedure A:

1. Deprotection: Removal of the t-butyloxycarbonyl-protecting group (Boc) was achieved by treatment of the resin with deblocking reagent (trifluoroacetic acid (TFA)/anisole/dichloromethane(DCM) 45:2.5:52.5 v/v containing 1 mg/mL of indole), two times for one minute and once for twenty minutes. The resin was then washed with DCM several times, followed by neutralization with base [10% diisopropylethylamine (DIEA) in DCM], three times for one minute. The resin was subsequently washed with DCM and dimethylformamide (DMF).

2. Coupling: All couplings and recouplings were mediated in the same manner. Boc-Oic (1.47 mmol, 0.4M in DMF) was mixed with one equivalent of diisopropylcarbodiimide (DIPCDI) (1.47 mmol, 0.4M in DCM) for a two minute activation period prior to coupling with the resin. The mixture was added to the reaction vessel containing the resin and mixed for two hours. Coupling efficiency of the amino acid to the growing peptide chain on the resin was checked. Incomplete coupling of an amino acid resulted in a recoupling step. Recoupling involved washing the resin-peptide three times for one minute with base followed by DCM and DMF. Amino acid activation with DIPCDI with addition to the peptide-resin was repeated and allowed to mix an additional two hours. After a successful coupling the peptide-resin was washed several times with DCM.

3. Capping: The growing peptide chain was capped on the α-amino group by acetylation with 1-acetylimidazole (0.3M in DMF) at the end of each coupling or recoupling. The resin was washed three times with base followed by DCM and DMF. The resin was treated with capping reagent for 30 minutes and then washed with DMF.

Procedure B:

The N-terminal protecting group was removed by the following procedure:

Terminal deprotection: Following the capping of the final amino acid to be added to the growing peptide chain, the peptide-resin was treated with deblocking reagent (TFA/anisole/DCM) twice for one minute and once for 20 minutes. The resin was washed with DCM followed by methanol and then dried by a stream of inert gas.

The following amino acids were added to the growing peptide chain according to the listed programs: Boc-D-Phe (A), Boc-Ser(Bzl) (A), Boc-Thi (A), Boc-Gly (A), Boc-4 Hyp(Bzl) (A), Boc-Pro (A), Boc-Arg(Tos) (A), Boc-D-Arg(Tos) (A), (B). This yielded 0.481 g of protected peptide-resin as the TFA salt.

HF Cleavage: The peptide-resin (0.481 g) was suspended in 5 mL of liquid anhydrous HF (ratio of 10 mL HF/g resin) containing 0.48 mL of anisole at −70° C. and stirred for 60 minutes at 0° C. The HF was removed by a stream of nitrogen gas followed by vacuum (water aspirator). The resin was washed three times with 30 mL of ethyl ether and dried under high vacuum for 30 minutes. The peptide was extracted with distilled deionized water (200 mL) and the solution was lyophilized to give 176 mg of crude deprotected peptide.

Purification: The peptide was purified on a reverse phase C-18 (2×25 cm) Vydac HPLC column using a gradient of 0.1% TFA/H20 and acetonitrile (0.1% TFA) to give 53 mg of purified deprotected peptide.

Analysis: Purified peptide was characterized by amino acid analysis and gave the following results: Arg, 2.9 (3.0); Ser, 0.92 (1.0); Thi, 1.09 (1.0); Gly, 1.0 (1.0).

The peptide was also characterized by mass spectrometry (JEOL HX110/110 FAB) [M+H] obsd 1308.7, [M=H] calcd 1308.6.

The invention being thus described, it will be obvious that the same may be varied in many ways. Such variations are not to be regarded as a departure from the spirit and scope of the invention and all such modifications are intended to be included within the scope of the following claims.

---

What is claimed is:

1. A peptide having the formula:

N-A-B-C-D-E-F-G-H-I-J-Cn wherein:

N is hydrogen;

A and B are independently selected from the group consisting of L-Arg, D-Arg, Lys-Lys, and Lys;

C, D and E are direct bonds;

F is $R^2$;

G is selected from the group consisting of Ser and Thr;

H is selected from the group consisting of D-Tic, D-Phe and D-Hypethers selected from a compound having the trans and D-configuration (*) and the formula:

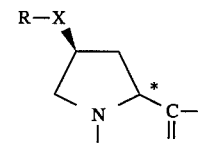

wherein

R is selected from the group consisting of $C_1-C_6$ alkyl, substituted $C_1-C_6$ alkyl, $C_2-C_8$ alkenyl, $C_3-C_8$ cycloalkyl, $C_3-C_8$ cycloalkyl substituted $C_1-C_6$ alkyl, an aryl group, an arylalkyl group, and a group of the formula $R^1NHC(O)$, wherein R is $C_1-C_6$ alkyl or aryl, and X is either sulfur or oxygen;

and pharmaceutically acceptable salts thereof;

I is selected from the group consisting of Oic, Phe, Tic, Azt and Hypethers selected from a material having the L-configuration (*) and the formula:

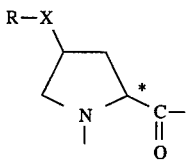

wherein

R is selected from the group consisting of $C_1-C_6$ alkyl, substituted $C_1-C_6$ alkyl, $C_2-C_8$ alkenyl, $C_3-C_8$ cycloalkyl, $C_3-C_8$, cycloalkyl substituted $C_1-C_6$ alkyl, an aryl group, an arylalkyl group, and a group of the formula $R^1NHC(O)$, wherein $R^1$ is $C_1-C_6$ alkyl or aryl, and X is either sulfur or oxygen, wherein the moiety R-X may be either cis or trans to the α-carboxyl residue, and pharmaceutically acceptable salts thereof;

J is selected from the group consisting of Arg and Lys;

Cn is a hydroxyl group;

and pharmaceutically acceptable salts thereof;

and wherein $R^2$ has the following formula wherein x is 3 to 15:

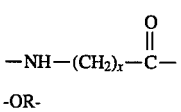

-OR-

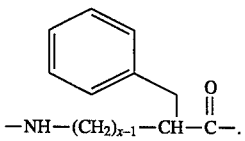

2. The peptide of claim 1 wherein:

N is hydrogen;

A is D-Arg;
B is Arg;
C, D and E are direct bonds;
F is selected from the group consisting of

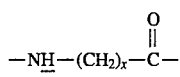

— AND —

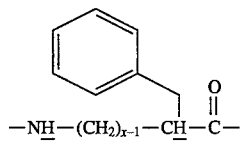

wherein
x is 3 to 15;
G is Ser;
H is D-Tic or D-Phe;
I is selected from the group consisting of Phe, Azt, and Tic;
J is Arg;
Cn is a hydroxyl group;
and pharmaceutically acceptable salts thereof.

3. The peptide of claim 1 wherein:
A is D-Arg;
B is Arg;
C, D and E are direct bonds;
F is selected from the group consisting of:

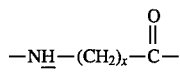

— AND —

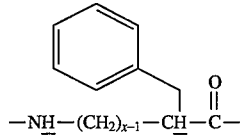

wherein
x is 4 to 12;
G is Ser;
H is selected from the group consisting of D-Tic and D-Phe;
I is selected from the group consisting of Oic, Tic, Azt and Phe;
J is Arg;
Cn is a hydroxyl group;
and pharmaceutically acceptable salts thereof.

4. A compound having the formula selected from the group consisting of:

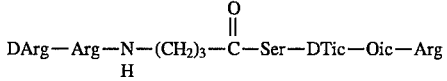

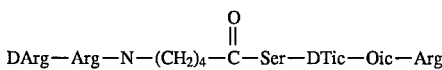

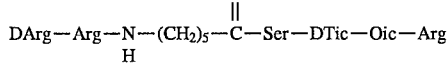

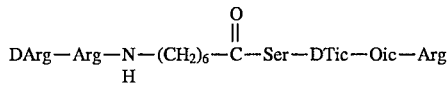

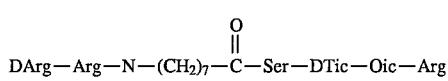

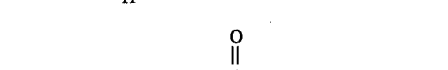

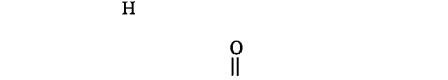

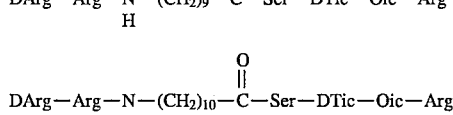

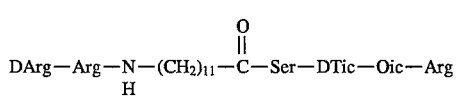

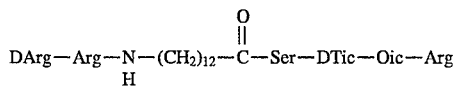

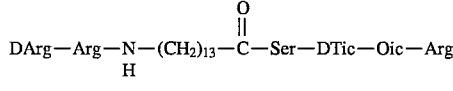

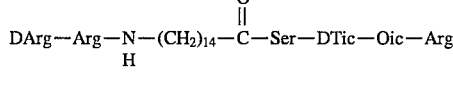

and

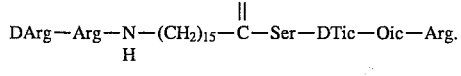

5. A compound having the formula selected from the group consisting of:

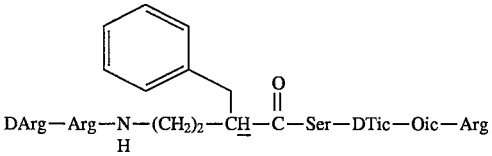

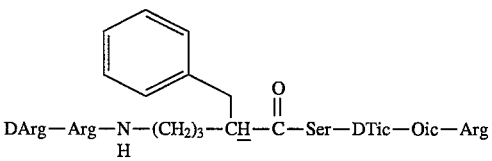

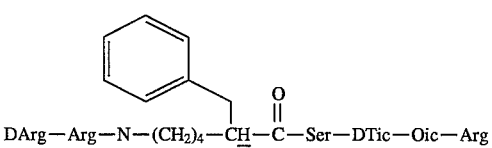

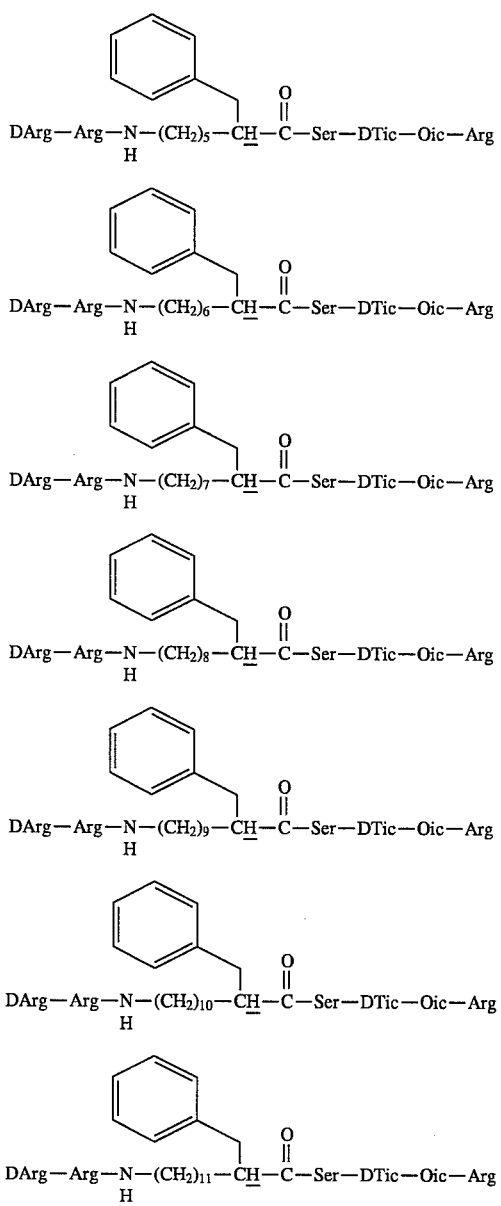

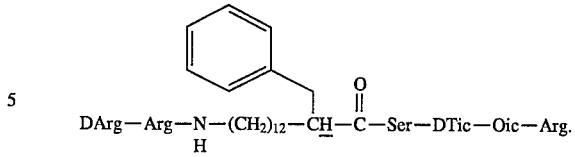

6. A pharmaceutical composition useful as a bradykinin receptor antagonist comprising a pharmaceutical carrier and an effective amount of the peptide of claim 1.

7. A pharmaceutical composition useful as a bradykinin receptor antagonist comprising a pharmaceutical carrier and an effective amount of the peptide of claim 4.

8. A pharmaceutical composition useful as a bradykinin receptor antagonist comprising a pharmaceutical carrier and an effective amount of the peptide as claim 5.

9. A pharmaceutical preparation for treating local pain and inflammation from burns, wounds, cuts, rashes or other trauma and pathological conditions caused by the production of bradykinin or related kinins by an animal, which comprises: an effective amount of the peptide of claim 1 to antagonize bradykinin and a suitable pharmaceutical carrier.

10. A pharmaceutical preparation for treating local pain and inflammation from burns, wounds, cuts, rashes or other trauma and pathological conditions caused by the production of bradykinin or related kinins by an animal, which comprises: an effective amount of the peptide of claim 4 to antagonize bradykinin and a suitable pharmaceutical carrier.

11. A pharmaceutical preparation for treating local pain and inflammation from burns, wounds, cuts, rashes or other trauma and pathological conditions caused by the production of bradykinin or related kinins by an animal, which comprises: an effective amount of the peptide of claim 5 to antagonize bradykinin and a suitable pharmaceutical carrier.

12. A process for treating local pain and inflammation, which comprises: administering an effective amount of the peptide of claim 1 to an animal in need thereof.

13. A process for treating local pain and inflammation, which comprises: administering an effective amount of the peptide of claim 4 to an animal in need thereof.

14. A process for treating local pain and inflammation, which comprises: administering an effective amount of the peptide of claim 5 to an animal in need thereof.

* * * * *

UNITED STATES PATENT AND TRADEMARK OFFICE
CERTIFICATE OF CORRECTION

PATENT NO.   : 5,521,158
DATED        : May 28, 1996
INVENTOR(S)  : KYLE et al.

It is certified that error appears in the above-indentified patent and that said Letters Patent is hereby corrected as shown below:

Column 26,
  line 5, "Ris" should read -- $R^1$ is --; line 43, the comma after "$C_3$-$C_8$" should be deleted.

Column 27,
  line 8, that portion of the formula reading "N$\underline{H}$" should read -- NH --;
  line 15, that portion of the formula reading "NH-$(CH_2)_{x-1}$-C$\underline{H}$" should read -- NH-$(CH_2)_{x-1}$-CH --.
  line 36, that portion of the formula reading "N$\underline{H}$" should read -- NH --;
  line 44, that portion of the formula reading "NH-$(CH_2)_{x-1}$-C$\underline{H}$" should read -- NH-$(CH_2)_{x-1}$-CH --.

Column 28,
  lines 52, 59 and 66, those portions of the formulas reading "C$\underline{H}$" should read -- CH --.

Column 29,
  lines 7, 13, 19, 26, 32, 39, 45, those portions of the formulas reading "C$\underline{H}$" should read -- CH --.

UNITED STATES PATENT AND TRADEMARK OFFICE
CERTIFICATE OF CORRECTION

PATENT NO. : 5,521,158
DATED : May 28, 1996
INVENTOR(S) : KYLE et al.

It is certified that error appears in the above-indentified patent and that said Letters Patent is hereby corrected as shown below:

<u>Column 30</u>,
   line 6, that portion of the formula reading "C$\underline{H}$" should read -- CH --.

Signed and Sealed this

First Day of October, 1996

Attest:

BRUCE LEHMAN

*Attesting Officer*      *Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 9 amino acid residues
( B ) TYPE: amino acid
( C ) STRANDEDNESS: Not Relevant
( D ) TOPOLOGY: unknown ( i i ) MOLECULE TYPE: peptide ( x i ) SEQUENCE DESCRIPTION: SEQ ID NO:1:

Arg Pro Pro Gly Phe Ser Pro Phe Arg
1               5